(12) United States Patent
Laugwitz (10) Patent No.: US 10,690,579 B2
(45) Date of Patent: Jun. 23, 2020

(54) GROUND COMPACTOR AND METHOD FOR DETERMINING SUBSTRATE PROPERTIES USING A GROUND COMPACTOR

(71) Applicant: BOMAG GMBH, Boppard (DE)

(72) Inventor: Niels Laugwitz, Lahnstein (DE)

(73) Assignee: BOMAG GMBH, Boppard (DE)

( * ) Notice: Subject to any disclaimer, the term of this patent is extended or adjusted under 35 U.S.C. 154(b) by 154 days.

(21) Appl. No.: 16/039,045

(22) Filed: Jul. 18, 2018

(65) Prior Publication Data
US 2019/0025175 A1 Jan. 24, 2019

(30) Foreign Application Priority Data
Jul. 18, 2017 (DE) .................... 10 2017 006 844

(51) Int. Cl.
| | |
|---|---|
| *G01N 9/36* | (2006.01) |
| *E01C 19/28* | (2006.01) |
| *E02D 1/02* | (2006.01) |
| *E02D 3/026* | (2006.01) |
| *G01N 33/42* | (2006.01) |

(Continued)

(52) U.S. Cl.
CPC ............ *G01N 9/36* (2013.01); *E01C 19/288* (2013.01); *E02D 1/022* (2013.01); *E02D 3/026* (2013.01); *G01N 33/42* (2013.01); *E01C 19/23* (2013.01); *E01C 19/231* (2013.01); *E01C 19/27* (2013.01); *G01N 2203/0019* (2013.01); *G01N 2203/0037* (2013.01); *G01N 2203/0085* (2013.01); *G01N 2203/0244* (2013.01)

(58) Field of Classification Search
CPC ........ E01C 19/23; E01C 19/231; E01C 19/27; E01C 19/288; G01N 2203/0019; G01N 2203/0037; G01N 2203/0085; G01N 2203/0244; G01N 9/36; G01N 33/42; E02D 3/026; E02D 1/022
See application file for complete search history.

(56) References Cited

U.S. PATENT DOCUMENTS

| | | | | |
|---|---|---|---|---|
| 6,973,821 | B2 * | 12/2005 | Corcoran | ............... E02D 3/026 73/78 |
| 8,671,760 | B2 * | 3/2014 | Wallrath | ............... E02D 3/046 73/594 |

(Continued)

FOREIGN PATENT DOCUMENTS

| | | |
|---|---|---|
| DE | 10335690 | 12/2004 |
| DE | 102005000641 | 9/2005 |

(Continued)

OTHER PUBLICATIONS

Search Report from corresponding German Appln. No. 10 2017 006 844.5, dated May 8, 2018.

(Continued)

*Primary Examiner* — Jonathan M Dunlap
(74) *Attorney, Agent, or Firm* — Grossman, Tucker, Perreault & Pfleger, PLLC (57) ABSTRACT

The present invention proposes a ground compactor with a ground compaction drum rotating about a rotation axis during compaction of a substrate, wherein the ground compaction drum includes a deformation sensor for detection of an elastic deformation of the ground compaction drum in order to determine a degree of stiffness of the substrate.

14 Claims, 4 Drawing Sheets

(51) Int. Cl.
    *E01C 19/23*    (2006.01)
    *E01C 19/27*    (2006.01)

(56) References Cited

U.S. PATENT DOCUMENTS

| | | | |
|---|---|---|---|
| 9,423,332 B2* | 8/2016 | Corcoran | .................. E01C 7/00 |
| 9,650,747 B2* | 5/2017 | Villwock | ................ E02D 3/039 |
| 2005/0183512 A1 | 8/2005 | Corcoran | |
| 2007/0150147 A1 | 6/2007 | Rasmussen et al. | |
| 2012/0134746 A1 | 5/2012 | Wallrath et al. | |
| 2015/0101424 A1 | 4/2015 | Villwock et al. | |
| 2016/0103051 A1 | 4/2016 | Corcoran et al. | |
| 2017/0159246 A1 | 6/2017 | Pistrol et al. | |
| 2018/0002882 A1* | 1/2018 | Stromsoe | ............. E01C 19/266 |

FOREIGN PATENT DOCUMENTS

| | | |
|---|---|---|
| DE | 102010052713 | 5/2012 |
| DE | 102013220962 | 4/2015 |
| DE | 112015004191 | 6/2017 |
| EP | 3176324 | 6/2017 |

OTHER PUBLICATIONS

Examination Report from related EPO Appln. No. 18000593.9, dated Nov. 26, 2018.

* cited by examiner

GROUND COMPACTOR AND METHOD FOR DETERMINING SUBSTRATE PROPERTIES USING A GROUND COMPACTOR

CROSS-REFERENCE TO RELATED APPLICATION

The present application claims priority to German Patent Application Serial No. 10 2017 006 844.5, filed Jul. 18, 2017, the disclosure of which is incorporated by reference herein in its entirety.

FIELD

The invention relates to a ground compactor, in particular a roller, with a ground compaction drum, which rotates about a rotation axis during compaction of a substrate, and an evaluation device. The invention further relates to a method for determining a degree of stiffness of a substrate using a ground compactor, in particular using a static or oscillating ground compaction drum.

BACKGROUND

Generic ground compactors are provided for compacting the substrate and are well known in the prior art, for example in the form of road rollers or, more specifically, tandem rollers with which a ground layer structure, and in particular an asphalt road including its foundation, can be compacted. Essential elements of a ground compactor, in particular a self-propelled ground compactor, include a machine frame, a drive engine, a driver's cab as well as front and rear ground compaction drums with respect to the working direction. To achieve compaction, the ground compactor is moved over the ground layer structure to be compacted in several steps, further compaction being achieved with each passage until a maximum compaction is reached. Upon reaching the maximum compaction, further compaction of the substrate is no longer necessary or is even detrimental since this will result in a loosening of the compacted ground layer structure or grain shattering. For this reason, it is helpful to know the current degree of compaction of the substrate. Moreover, an aspect of particular importance when employing ground compaction rollers is the formation of bow waves. Due to the drum sinking into the substrate to a greater or lesser extent, ground material is displaced in a circumferential direction toward the front and the rear of the drum. The amount of material accumulated in front of the drum can become so large that, due to the displacement resistance, it is no longer pushed ahead of the drum but is rolled over by the same. This leads to an unevenness in the road surface.

Besides static ground compactors, with which ground compaction is achieved exclusively by the weight of the ground compaction drum, dynamic ground compactors are known in the art with which, in order to increase the compaction performance, the ground compaction drum not only rotates about a rotation axis when rolling over the substrate but also performs an additional movement in order to affect a transfer of grains in the substrate into a layer with a higher density. A distinction is made here between vibrating and oscillating ground compaction drums. With oscillating ground compaction drums, the rotational movement of the ground compaction drum in the direction of rotation is superimposed by an oscillating movement, resulting in a shearing force being exerted by the ground compaction drum on the surface of the substrate. This oscillating movement is normally caused by two oscillating masses rotated inside the ground compaction drum. In the case of vibrating ground compaction drums, the ground compaction drum enters a vibrating state in which the ground compaction drum performs a vibrating movement, whereby the ground compaction drum exerts a contact force on the substrate, said contact force being directed towards the substrate and time-modulated due to the vibrating movement. Due to the time modulation of the contact force and the resulting time-variable deformation of the substrate, the change in the contact force that occurs with vibrating ground compaction drums can be utilized for determining the degree of stiffness of the substrate, as is known, for example, from DE 10 2010 052 713 A1, said degree of stiffness being a measure of the compaction in the substrate. Since static ground compactors lack such a time-modulated contact force, the known methods for determining a degree of stiffness for vibrating ground compaction equipment cannot be transferred to static ground compactors. Although time-variable thrust forces do occur in ground compactors with an oscillating ground compaction drum, these forces mainly depend on the friction conditions between the drum and the substrate and are consequently rather ill-suited for ascertaining ground stiffness.

SUMMARY

Therefore, it is an object of the present invention to provide a ground compactor suitable for determining a current degree of stiffness of the substrate and thus the current degree of ground compaction without requiring a vibrating ground compaction drum. In particular, it is an object of the present invention to provide a ground compactor with an oscillating or static ground compaction drum that can detect the degree of stiffness of the substrate during operation in spite of the oscillating or static ground compaction drum. Another object of the present invention is to prevent uneven road surfaces caused by too large bow waves in front of the drum.

Specifically, the invention proposes arranging a deformation sensor for detecting an elastic deformation on the ground compaction drum in order to infer the degree of stiffness of the substrate from the detected elastic deformation of the ground compaction drum. The ground compactor includes an evaluation device for evaluating the measurement results, said evaluation device being configured, for example, as a computing unit, and in particular as an on-board computer, or as a part of the on-board computer of the ground compactor. According to the invention, the ground compaction drum includes a deformation sensor for detecting an elastic deformation of the ground compaction drum and the evaluation device is configured to determine the degree of stiffness of the substrate and/or the shape of a bow wave preceding the ground compaction drum in a working direction and/or the shape of a depression trough of the ground compaction drum based on the position of a point on a circumference of the ground compaction drum where the deformation sensor measures the largest deformation. The deformation sensor is thus configured in particular to ascertain a maximum value of the deformation of the ground compaction drum and to transmit its position to the evaluation device. The position transmitted by the deformation sensor can refer to the position of the point of maximum deformation within the measuring range of the deformation sensor or to the position with respect to a rotation angle of the ground compaction drum. In the first case, the position with respect to the rotation angle is measured by means of an additional determination of the rotation angle as described below. An essential aspect here is that contact with the substrate will cause not only a deformation of the substrate but also a deformation, in particular an elastic deformation, of the ground compaction drum, and that this deformation changes in accordance with the state of contact between the ground compaction drum and the substrate. As the contact state in turn depends on the stiffness of the substrate, information about the degree of stiffness of the substrate can be obtained indirectly by monitoring the deformation of the drum. Generally, the term "contact state" here is to be understood as a collective term for all the factors relating to the contact between the substrate and the ground compaction drum. The contact state is, for example, characterized by a contact area formed by the contact between the substrate and the ground compaction drum, said contact area becoming smaller with increasing substrate stiffness, as the drum sinks into the ground substrate to a lesser extent. The contact area thus narrows with increasing stiffness in particular in a direction determined by the direction of rotation of the ground compaction drum. As these defining influences of the contact state occur in every ground compaction drum, the ground compactor according to the invention allows a determination of the degree of stiffness without requiring a vibrating ground compaction drum. Specifically, the invention proposes finding the point on the circumference of the ground compaction drum where the elastic deformation of the ground compaction drum is largest when passing over the substrate. The position of this point depends on the contact state, i.e. the shape of the contact area between the ground compaction drum and the ground substrate. It is the point where the deformation of the ground compaction drum reaches a local maximum. The angle, i.e. the rotation angle of the ground compaction drum that describes the position of this point, is also referred to below as the critical rotation angle. The invention is based on the finding that the position of the point of maximum deformation of the ground compaction drum increasingly approaches the lowest vertical point of the ground compaction drum as the compaction of the substrate increases. In other words, the point of maximum deformation of the ground compaction drum approaches a point on the circumference of the ground compaction drum located vertically below the rotation axis of the ground compaction drum as the stiffness of the substrate increases. This correlation allows inferences regarding the contact state, i.e. the shape of the contact area between the ground compaction drum and the substrate, and thus regarding the stiffness of the substrate, based on the position of said point. The ground stiffness can then be used as an indicator of an achieved compaction, i.e. conclusions can be drawn regarding a compaction state of the ground underneath from the determined ground stiffness, e.g. by using an elastic modulus, the vibration behavior and/or the density of the material of which the ground layer is made. In particular, it is also conceivable here to also consider the asphalt temperature during the compaction process in order to determine the degree of compaction. Moreover, in particular the elastic deformation is monitored during the operation of the ground compactor. This allows a determination of the degree of stiffness without requiring an interruption of the ground compaction. A corresponding calculation of the substrate stiffness can be based on the measured deformations or the position of the point of maximum deformation. This, however, requires a precise knowledge of the actual drum geometry including manufacturing tolerances. As an alternative to a direct calculation, the determination of the degree of compaction can thus also be made by means of characteristic diagrams created for the respective ground compactor. Such characteristic diagrams are thus compiled in advance and are stored, e.g., electronically in the on-board computer of the ground compactor. The characteristic diagrams describe in particular the correlation between the ground stiffness and the position of the point of maximum deformation. Based on the measured position, the ground stiffness or the degree of compaction of the ground can thus be inferred from the characteristic diagrams during the operation of the ground compactor. As already mentioned, a local maximum of the measured values ascertained by the deformation sensor can be used for ascertaining the position of the point of maximum deformation. The point of maximum deformation is preceded and succeeded, both temporally and spatially within the measuring range of the deformation sensor, by local minima of the measured values of the deformation sensor due to an opposite deformation. As an alternative to the determination of the maximum, it is also possible to ascertain the position of these local deformation minima via the deformation sensor. As the point of maximum deformation is located approximately centrally between the two minima, the position of the point of maximum deformation can be inferred from the position of the minima. Moreover, the contact zone between the ground compaction drum and the substrate is proportional to the distance between the two minima The width of the contact zone can thus be estimated based on the position of the two minima By means of a comparison with characteristic diagrams specified in advance, conclusions as to the substrate stiffness and/or the penetration depth of the ground compaction drum can also be drawn from the width of the contact zone. As an alternative to the described minima, the zero crossing of the deformation may also be used. The zero crossing corresponds to the points where the deformation measured by the deformation sensor changes from a negative to a positive deformation. Such points also precede and succeed the maximum in an essentially symmetrical manner.

Alternatively or additionally, the detected position of the point of maximum deformation can be used for inferring the shape, in particular the size and/or extension, of the bow wave preceding the ground compaction drum in the working direction. The so-called bow wave is another defining factor of the contact state. It refers to a material accumulation occurring directly in front of the ground compaction drum in the working direction, the size of which decreases as the stiffness of the substrate increases. This bow wave in turn creates a rolling resistance which can also influence the deformation character of the ground compaction drum. The influence of the rolling resistance caused by the bow wave on the contact state and, consequently, on the elastic deformation of the ground compaction drum diminishes as the size of the bow wave decreases. As a result, the influence of the bow wave on the deformation character becomes independent of the direction of travel. The vehicle operator is preferably informed of the current form of the bow wave so that he can take appropriate countermeasures, if necessary—e.g. when changing working direction—in order to avoid leaving behind an unevenness in the ground surface in the form of the bow wave. Possible measures are the use of a roller with a lower weight, reduction of the compaction energy supplied or allowing the cooling of the hot mixed asphalt material so that its deformation resistance increases. If the bow wave is small enough so that there is little risk of the formation of unevenness, the compaction power can be increased, e.g. by the application of vibration. It is also conceivable to infer a shape, in particular a depth, of a depression trough and subsequently, indirectly via the depression trough, the degree of compaction from the position of the point of maximum deformation. Alternatively or additionally, the average rotational speed of the drum can be ascertained by means of the determination of the time intervals between the deformation maxima. Accordingly, e.g. the approximate width of the deformation zone can be ascertained without measuring the rotation angle with a corresponding sensor. A constant vehicle speed, which is frequently the case in practice, is assumed here. If there are sudden large deviations in the period duration of the deformation maxima, a reversing operation can be assumed and the measurement result is discarded. As the detection of the deformation maximum requires a very high scanning rate and, moreover, can be affected by random disturbances of the measuring signal, the gradient dε/dφ before and after the maximum can also be ascertained. The gradient dε/dφ is lower at lower substrate stiffness levels than it is at higher substrate stiffness levels. Similarly, the extension of the contact zone can be characterized by the distance between the local minima of the drum deformation.

In principle, a deformation of the ground compaction drum is to be understood to mean any change in shape undergone by the ground compaction drum during the rotating movement about the rotation axis during a compaction operation. Specifically, the deformation is understood to mean the change in shape undergone by the ground compaction drum due to the contact between the substrate and the ground compaction drum when the latter rolls over the former. The change in shape here preferably occurs mostly on the circumference of the ground compaction drum, i.e. in the drum shell. A typical deformation can be, e.g., a bending, in particular a local extension or compression, of the ground compaction drum.

The ground compaction drum preferably comprises an essentially hollow, cylindrical drum shell with an inner side facing the rotation axis, the deformation sensor being arranged on said inner side of the drum shell. The deformation sensor is thus arranged in a protected manner on the side of the ground compaction drum facing away from the substrate in the region where the deformation occurs. For quick access, e.g. for maintenance purposes, the deformation sensor is preferably arranged in an end region of the ground compaction drum and at a distance of less than 25 cm, preferably less than 15 cm, and especially less than 10 cm, from one of the face sides or outer edges of the ground compaction drum. An essentially unobstructed access to the deformation sensor permits a removal of the deformation sensor from the ground compaction drum or the fastening of the deformation sensor to the ground compaction drum, as required. The ground compactor preferably comprises a releasable coupling mechanism with which the deformation sensor can be readily released from or mounted on the ground compaction drum, e.g. a screw connection. Furthermore, the ground compactor preferably comprises a front ground compaction drum and a rear ground compaction drum with respect to the working direction, each comprising a deformation sensor. It is also conceivable that the deformation sensor is arranged on a cup washer of the drum.

In order to improve the spatial resolution, several deformation sensors are preferably provided. By means of a system comprising several deformation sensors, the number of measuring points can be advantageously increased. For example, the position of the point of maximum deformation of the ground compaction drum can be ascertained with a correspondingly higher frequency per revolution of the ground compaction drum if multiple deformation sensors are distributed in the circumferential direction. In this manner, changes in the stiffness of the ground can be detected faster.

Further, if two drums are used, it is possible that deformation sensors are respectively arranged on a front drum in relation to the working direction and a rear drum in relation to the working direction so that an increase in compaction caused by the front drum can be ascertained using the deformation sensor on the rear drum. In accordance with this approach, a motion profile of the ground compactor, e.g. a motion in a crab-steering mode, is preferably also considered.

In order to detect the deformation, in particular the essentially elastic deformation, of the ground compaction drum occurring during the compaction process, it is sufficient to monitor a local region of the ground compaction drum, preferably continuously, with regard to the deformation experienced by said local region during a full revolution of the ground compaction drum. As a result of its arrangement within a section of the ground compaction drum, the deformation sensor will measure a deformation that can be used for the determination of the degree of stiffness at least once during a full revolution. According to the invention, the change in deformation within a full revolution is measured as a function of the rotation angle of the ground compaction drum, whereby the position of the point of maximum deformation can be ascertained. The angular position of the ground compaction drum can be ascertained in any way known in the prior art. To this end, the ground compactor preferably comprises a measuring device with which the rotation angle of the ground compaction drum can be detected, in particular in order to be able to ascertain the position of the deformation sensor relative to the ground substrate. The measuring device for determining the rotation angle can be, e.g., a rotational rate sensor or an accelerometer, in particular a two-axis accelerometer. It is also conceivable to utilize a pulse generator for determining the rotation angle. The pulse generator here provides a certain number of digital pulses per revolution so that the rotation angle is ascertained by counting the pulses. In accordance with a particularly simple approach for determining the rotation angle when motion is constant, i.e. when the drum rotates at an essentially constant speed, a maximum deformation occurs at regular time intervals so that, if a single deformation sensor is used, the current rotation angle can be inferred from the measured amplitude and the angular speed. In principle, the determination of the rotation angle acts as a measure for the orientation of the ground compaction drum during its rotation, wherein the specific orientation of the ground compaction drum during a full revolution is clearly associated with exactly one rotation angle. For example, the rotation angle, in particular the angle 0°, is set by the position of the deformation sensor.

In principle, any deformation sensor with which an elastic deformation of the ground compaction drum can be detected can be employed in the context of the invention. For example, it is conceivable that a transverse strut extends inside the ground compaction drum and that a pressure force is exerted on said transverse strut in the case of an elastic deformation, which pressure force in turn can be measured, or that a customized camera system is used for determining the elastic deformation. In a preferred embodiment, a strain sensor is recessed into the ground compaction drum or placed on the inner side of the drum shell. The strain sensor can be, for example, a piezoelectric strain sensor in which a force acting on a piezoelectric element, e.g. a tensile force caused by the strain, causes a tension which can be detected and used as a measured value for the strain of the drum. Generally, the strain sensor comprises in particular at least one strain gauge, a strain transformer, a fiber Bragg grating, etc. The use of such a strain sensor, in particular a strain sensor configured as a strain gauge, is advantageous in that it can be attached to the inner side of the drum shell in a relatively flat manner and accordingly does not occupy much installation space inside the ground compactor, i.e. the ground compaction drum. Also, strain sensors are particularly well-suited for measuring strains resulting from an elastic deformation occurring as a result of the contact between the substrate and the ground compaction drum when the latter rolls over the former. During a full revolution, the strain sensor will provide relevant measurement results while being guided past the contact region during the rotating movement of the ground compaction drum. In particular, the strain that occurs along a direction determined by the direction of rotation of the ground compaction drum is monitored. It is conceivable here that the strain sensor is activated for a specified range of rotation angles and switches to a stand-by mode when outside the specified range of rotation angles.

In principle, the position of the point of maximum deformation of the ground compaction drum can be ascertained in different ways. According to a preferred embodiment, a particularly precise measurement is achieved when the evaluation device is configured to use a rotation angle spanned by a straight line intersecting the rotation axis and the point of maximum deformation of the ground compaction drum and a reference line, e.g. a horizontal or a vertical line, for ascertaining the degree of stiffness of the substrate and/or the shape of the bow wave and/or the shape of the depression trough. In particular the direction of the gravity vector can be ascertained as a vertical reference line particularly reliably and easily, e.g. with a two-axis accelerometer, and thus constitutes a suitable reference line for ascertaining the position of the point of maximum deformation. The position of the point of maximum deformation is then expressed by the angle between the vertical reference line and a connection line between the rotation axis of the ground compaction drum and the point of maximum deformation. This angle is in particular proportional to the depth of the depression trough, i.e. the height difference of the ground before and after the ground compaction drum in the working direction, as will be described in greater detail below.

According to the invention, the ground compactor comprises an evaluation device in order to provide a user with the measured deformation and/or the position of the point of maximum deformation and/or the ascertained values regarding ground stiffness or compaction and/or the bow wave and/or the depression trough in a user-friendly manner By means of such an evaluation device, e.g. the dependence of the deformation measured by the deformation sensor on the rotation angle can be depicted on a display apparatus. The display apparatus is preferably arranged on the operator platform so that a user or vehicle operator acquires information about the degree of stiffness of the substrate without having to leave the operator platform. It is further conceivable that the ground compactor has an input device and a storage device. This way, it is preferably possible to store measured deformations, in particular as a function of the rotation angle, together with comments regarding, e.g. information about ground composition, outside temperature or a particularity regarding the detection of the elastic deformation. Consequently, by means of the storage device, a database can be compiled which can be referred to for future determinations of degrees of stiffness.

In a particularly preferred embodiment, the ground compactor is a ground compactor with a static or oscillating ground compaction drum. The oscillating ground compaction drum preferably comprises two rotatable oscillating masses arranged inside the ground compaction drum. These two oscillating masses rotate in the same direction about two imbalance axes; moreover, they preferably have corresponding mass distributions and rotate about their respective imbalance axes in an offset manner during operation, in particular with a phase shift of 180°. The imbalance axes are arranged here as a pair and opposite one another and the rotation axis of the drum is located centrally between the imbalance axes.

According to another embodiment of the present invention, the ground compactor is a tandem roller. The characteristic feature of tandem rollers is that they have front and rear ground compaction drums Ideally, a deformation sensor is provided in the manner described above on at least one and preferably on both ground compaction drums.

The object is also achieved with a method for determining a stiffness of the substrate using a ground compactor in accordance with the explanations provided above. All features described above in relation to the ground compactor in accordance with the invention and their advantages apply analogously to the method in accordance with the invention and vice versa.

Specifically, the invention proposes detecting, in a first measuring step, an elastic deformation in at least a section of the ground compaction drum and the position of a point on a circumference of the ground compaction drum where the largest deformation occurs, wherein the degree of stiffness of the substrate and/or the shape of a bow wave preceding the ground compaction drum in a working direction and/or the shape of a depression trough of the ground compaction drum is determined from the position of said point. For this purpose, the ground compactor is guided over a substrate to be compacted with its ground compaction drums rotating about their rotation axes. The detection of the position of the point of maximum deformation and thus the determination of the degree of stiffness take place during operation, i.e. as the ground compactor rolls over the substrate. In particular, the deformation that is produced by the contact between the ground compaction drum and the substrate is detected. To this end, the deformation near the contact region defined by the contact between the ground compaction drum and the substrate is preferably detected, i.e. measured. The deformation is also detected once per revolution of the ground compaction drum, in particular when the deformation sensor is guided past the contact area.

A strain measurement in a local region of the ground compaction drum has proven suitable for detecting the extent of the elastic deformation in the ground compaction drum, i.e. the position of the point of maximum deformation. A strain sensor is provided for the measurement of the strain, use being made here of the fact that the elastic deformation is accompanied by a strain along a direction determined by the direction of rotation. This strain can be detected with the strain sensor in a simple manner Another advantage is that strain sensors are relatively small so that a strain sensor is a space-saving option for detecting the deformation. If the strain sensor is arranged on the inner side of the drum shell, the strain sensor is guided relatively closely past the contact region once per full revolution. It is further conceivable that the strain sensor is arranged in a recess within the ground compaction drum.

According to the invention, the elastic deformation is used as a function of the rotation angle in order to determine the degree of stiffness of the substrate. It is not necessary here to always measure the rotation angle of the ground compaction drum separately as e.g. several travel drive systems already include equipment providing information about the angle of rotation. In order to increase measuring accuracy, it can alternatively be provided that, in addition to the elastic deformation, a angle of rotation is detected separately in a second measuring step, e.g. by means of a rotational rate sensor or an accelerometer.

Besides the described use of a critical rotation angle at which the measured strain assumes a local maximum, it is in particular possible to utilize a gradual progression of the measured strain as a function of the rotation angle and/or an absolute value of the measured maximum strain in order to increase the measuring accuracy regarding the degree of stiffness.

BRIEF DESCRIPTION OF THE DRAWINGS

The invention will be explained in greater detail below with the help of the embodiment shown in the figures, which show schematically.

DETAILED DESCRIPTION

Identical elements are designated by identical reference numerals in the figures. Some recurring elements may not be designated separately in each figure.

Figure 1:
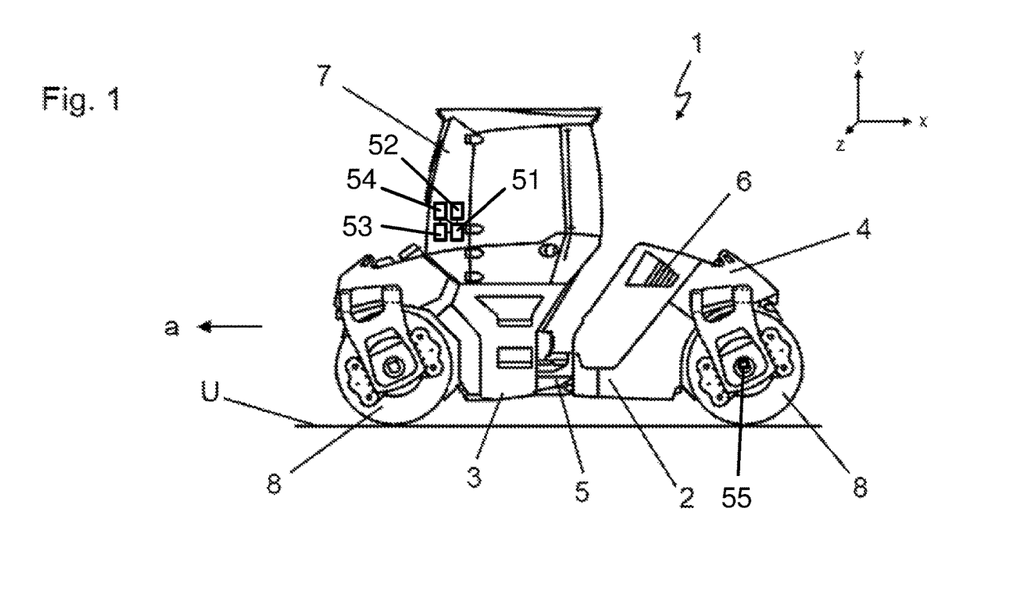
FIG. 1 is a side view of a ground compactor in the form of a tandem roller.

FIG. 1 shows a self-propelled ground compactor 1, more specifically a tandem roller. Essential elements of the roller include a machine frame 2 with a front frame 3 and a rear frame 4 connected to one another via an articulated joint 5, a drive engine 6, a driver's cab 7 as well as front and rear ground compaction drums 8 with respect to the working direction a. During operation, the roller 1 travels in or against the working direction a over the substrate U to be compacted by rolling over the substrate U with the two ground compaction drums 8. It goes without saying that other ground compactors 1 will also to be able to be configured in the manner described below, e.g. ground compactors with pivot steering, etc.

Figure 2:
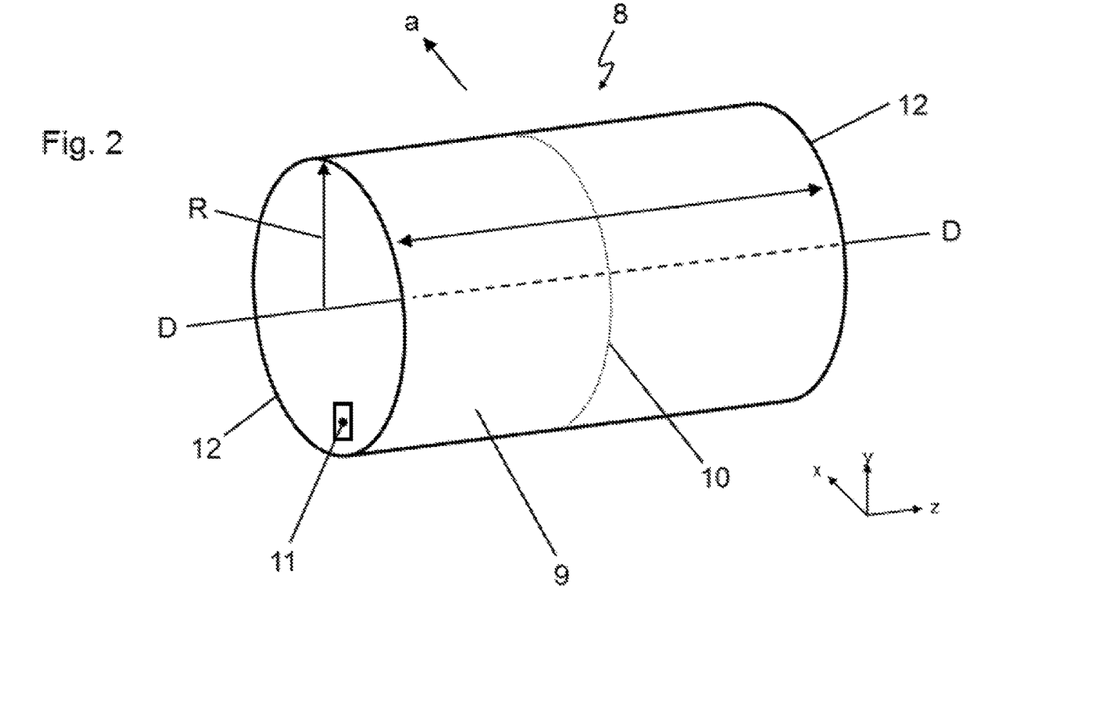
FIG. 2 is an oblique perspective of a drum shell of the ground compactor shown in FIG. 1.

The ground compaction drums 8 include an essentially hollow, cylindrical drum shell 9, as schematically represented in FIG. 2. During operation, the ground compaction drum 8 rotates about its rotation axis D, which extends horizontally and perpendicularly to the working direction a. The ground compaction drum 8, i.e. the drum shell 9, has a width B along the axis D, as well as a radius R. The drum shell 9 can be configured as a single piece or it can consist of two drum segments, as indicated by the dashed line 10 in FIG. 2. The drum shell 9 encloses a drum interior delimited in the radial direction by the drum shell 9. In the direction of the rotation axis D, the drum interior extends on both sides towards the respective face sides or in the radial direction towards the outer edges 12 of the drum shell 9.

An essential task of the drum consists in the compaction of a substrate U, in particular a substrate U of an asphalt road. To this end, the ground compactor 1 usually moves over the substrate U to be compacted in several working steps until a desired degree of compaction up to a maximum compaction of the substrate U has been accomplished. Upon reaching the maximum compaction, further compaction of the substrate U is no longer required or is even detrimental since this will result in a loosening of the compacted ground layer structure. In this respect, it is helpful to have knowledge of the current degree of compaction of the substrate U during operation in order to enable an efficient and reliable compaction process.

In the case of ground compactors 1 with a vibrating roller, the compaction power is increased by putting the ground compaction drum 8 into a vibrating state, in which the ground compaction drum 8 performs a vibrating movement. By this means, the ground compaction drum 8 exerts a contact force on the substrate U the amplitude of which is time-modulated in accordance with the vibrating movement. Said exertion occurs in a contact region between the ground compaction drum B and the substrate U along an essentially vertical direction, i.e. a direction perpendicular to the surface contour of the substrate U. The vibrating state of the ground compaction drum 8 here is initiated by means of oscillating masses which are rotated inside the ground compaction drum 8 in a manner known in the prior art during operation and which are specifically designed for generating an imbalance and the desired vibrating state.

In the case of a circular exciter, the vibration is effected by means of an oscillating mass rotating about the rotation axis R of the ground compaction drum 8, whereas in the case of an opposite exciter the ground compaction drum 8 is placed in the vibrating state by two counter-rotating oscillating masses. For such vibration rollers, the contact force acting vertically on the substrate U in a time-modulated manner can be used for determining a degree of stiffness, which in turn can be used as a measure of the degree of compaction of the substrate U.

Unlike the ground compactors 1 with vibration rollers described above, the ground compactors 1 with a static or oscillating ground compaction drum 8 described here lack a time-modulated contact force directed vertically towards the substrate U, which might be used for determining the substrate stiffness. In the case of ground compactors 1 with a static ground compaction drum 8, the compaction is effected exclusively by the static weight of the ground compaction drum 8. In the case of an oscillating ground compaction drum 8, the actual rotating movement of the ground compaction drum 8 about the rotation axis R is superimposed by an oscillating movement through which shearing forces are transferred to the substrate U which increase the compaction performance The oscillating movement superimposing the rotating movement is created, e.g., by two oscillating masses, wherein a first oscillating mass is arranged along a vertical direction above the rotation axis R and a second oscillating mass is arranged along the vertical direction beneath the rotation axis R. During operation, the first and second oscillating masses are rotated in the same direction inside the ground compaction drum 8. An advantage of oscillating ground compaction drums over vibration rollers is that the ground compactors 8 cause less vibrations in the environment of the machine. Damage to surrounding buildings or on bridges can thus be prevented.

According to the invention, in order to enable the determination of the degree of stiffness of the substrate U also when using ground compactors 1 with a static or oscillating ground compaction drum 8, an elastic deformation of the ground compaction drum 8 is identified during operation. To this end, the ground compaction drum 8 comprises a deformation sensor 11. The degree of stiffness of the substrate U is then inferred from the position of the point R (see FIGS. 5 and 6) of a measured maximum deformation on the shell of the ground compaction drum 8, in particular in combination with the change in the measured deformation and/or the change in deformation as a function of a rotation angle 101 of the ground compaction drum. Such an inference regarding the degree of stiffness of the substrate U is possible insofar as a change of a contact state between the substrate U and the ground compaction drum 8 results in a change of the elastic deformation of the ground compaction drum 8 and thus the position of the point R of measured maximum deformation. Due to the changing contact state between the substrate U and the ground compaction drum 8 depending on the degree of stiffness of the substrate U, an indirect conclusion regarding the degree of stiffness of the substrate U can thus be drawn in an advantageous manner via the position of the point R. The use of the position of the point R of maximum deformation according to the invention provides a particularly precise measurement of the ground properties.

Changes of the contact state resulting in a change in the elastic deformation include, e.g., a reduction of the contact region between the substrate U and the ground compaction drum 8, which can be observed as the level of ground compaction increases. It is observed here that this reduction of the contact region occurs along a direction determined by the circumferential direction of the ground compaction drum 8. The reduction of the contact region results in an increase in maximum contact pressure acting on the substrate U, which ultimately also influences the elastic deformation of the ground compaction drum 8. Furthermore, the contact state, which is relevant for the elastic deformation, is influenced by a bow wave forming in front of the ground compaction drum 8 in the working direction a. This bow wave becomes smaller with increasing ground stiffness, thus reducing a dependence of the contact state, and thus the detectable deformation, on a travel direction in which the ground compactor is guided over the substrate U. All these factors influence the position of the point R of measured maximum deformation on the ground compaction drum 8, which is why said point can be utilized as a reference.

A deformation sensor 11, preferably a strain sensor, is provided for the detection of the elastic deformation in the ground compaction drum 8. By means of the strain sensor, an elastic deformation can be identified in a local region of the ground compaction drum 8 in an advantageous manner To this end, the strain sensor 11 is arranged, e.g., on an inner side of the drum shell 9. In order to facilitate access to the strain sensor 11, e.g. for replacement or maintenance purposes, the strain sensor 11 is preferably arranged in the region of one of the face sides, i.e. the outer edge 12, of the drum shell 9. Further, the strain sensor 11 is preferably arranged in such a manner that the strain sensor 11 senses a strain in the ground compaction drum 8 along the direction of rotation. The strain sensor 11 ascertains the point R, in particular with respect to the circumference of the ground compaction drum 8, where the deformation of the ground compaction drum 8 is at a maximum. This can occur, e.g., with respect to the place of installation of the deformation sensor 11 on the ground compaction drum 8. The strain sensor 11 ascertains the point R within its measuring range on the circumference of the ground compaction drum 8. The rotation angle (a) at which the point R is located on the circumference of the ground compaction drum 8 can be ascertained from this measurement and information about the rotation state or rotation angle of the ground compaction drum 8. The rotation state or rotation angle of the ground compaction drum 8 can be knowable, for example, through the use of propulsion systems that provide such information. Besides the deformation sensor 11, the ground compactor 1 comprises in particular a measuring device 55 for determining the rotation angle 101. This measuring device 55 permits the depiction of the measured deformation values, in particular the measured strain values 102, as a function of the rotation angle 101, and in particular the determination of the position of the point R of maximum deformation on the shell of the ground compaction drum 8. The rotation angle 101 here is understood to mean a measure of the orientation of the ground compaction drum 8 rotating about the rotation axis R, wherein in particular any possible orientation of the ground compaction drum 8 can be associated with a particular rotation angle 101 between 0 and 360°. The rotation angles 101 here are preferably associated in such a way that the angle 0° is associated with the orientation of the ground compaction drum 8 in which the deformation sensor 11, in particular the strain sensor, is closest to the substrate U.

It is further conceivable that the deformation sensor 11 comprises a communication device, preferably a communication device for wireless communication, with which the detected measured values representing the strain of the ground compaction drum 8 are transmitted to an evaluation device 51. In the evaluation device 51, the recorded measured values are analyzed and provided to a user, e.g. on a display device 52. It is further conceivable that the ground compactor 1 comprises a storage device 54. Such a storage device 54 allows the storage of the measured or analyzed measured values and thus the compilation of a portfolio of empirical values consisting of measured deformations 102, e.g. for different types of substrates and/or asphalt temperatures. Comments concerning, e.g., the type of substrate, the asphalt temperature and/or peculiarities can be stored as additional information by means of an input device 53.

Figure 3:
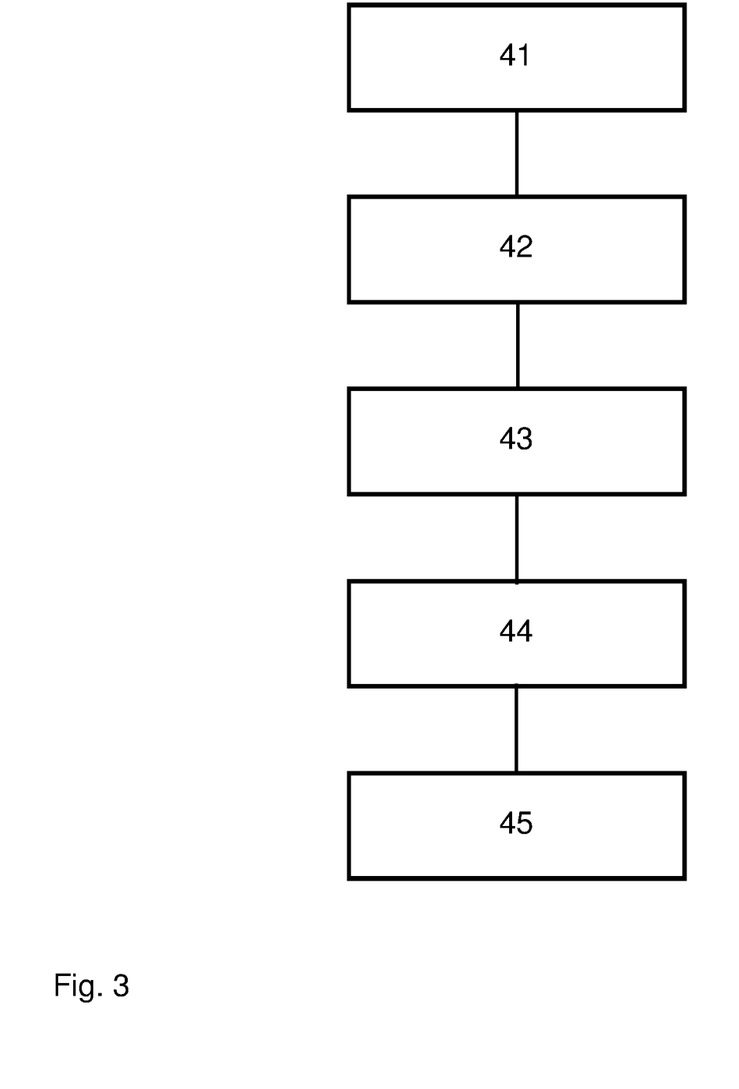
FIG. 3 is a method for determining a degree of stiffness in a substrate depicted as a flow chart.

The operational procedure for determining the degree of stiffness using a ground compactor 1, in particular a ground compactor as shown in FIG. 1, will be explained below with the help of the flow chart depicted schematically in FIG. 3. Essential steps of the method are: moving 41 a ground compactor 1 with a ground compaction drum 8 over the substrate U and rotating 42 the ground compaction drum 8 about a rotation axis R. In a first measuring step 43, the deformation of the ground compaction drum 8 is monitored by means of a deformation sensor 11 in order to detect an elastic deformation of the ground compaction drum 8. In this regard, the deformation is in particular detected or measured continuously, i.e. in an essentially uninterrupted manner If a strain sensor is used to observe a local region of the ground compaction drum 11 for a possible strain, the strain sensor will sense a significant change in strain once during a full revolution of the ground compaction drum 8 about the rotation axis R, in particular within an interval of the rotation. Based on these values, the deformation sensor 11 or the evaluation device 51 ascertains the position of the point R of maximum deformation. By means of a rotation angle 101 recorded in the second measuring step 43, it is possible to depict the measured deformations as a function of the current rotation angle 101 in an evaluation step 45. The rotation angle 101 here can either be measured separately or provided, e.g., by the drive system. As a result of the dependence of the measured deformation on the rotation angle 101, it is possible to register changes regarding the deformation behavior of the ground compaction drum 8 and to ascertain the position of the point R of maximum deformation also with regard to a rotation angle of the ground compaction drum 8. It is conceivable here that the dependence of the measured strain 102 is plotted graphically for the user of the ground compactor 1 and the user draws conclusions regarding the degree of stiffness of the substrate U based on his experience and his knowledge of the current compaction process, e.g., with regard to the ground conditions. Alternatively, it is also conceivable that the evaluation device 51 compares the measured dependence of the elastic deformation on the rotation angle 101 with reference data from a database and, after this evaluation, provides the user with a parameter as a measure of the degree of stiffness. It is also conceivable that the evaluation device issues a warning signal, e.g. an acoustic and/or visual warning signal, if a result of the evaluation step 45 indicates the desired degree of stiffness of the substrate U, i.e. a targeted ground compaction.

Figure 4A:
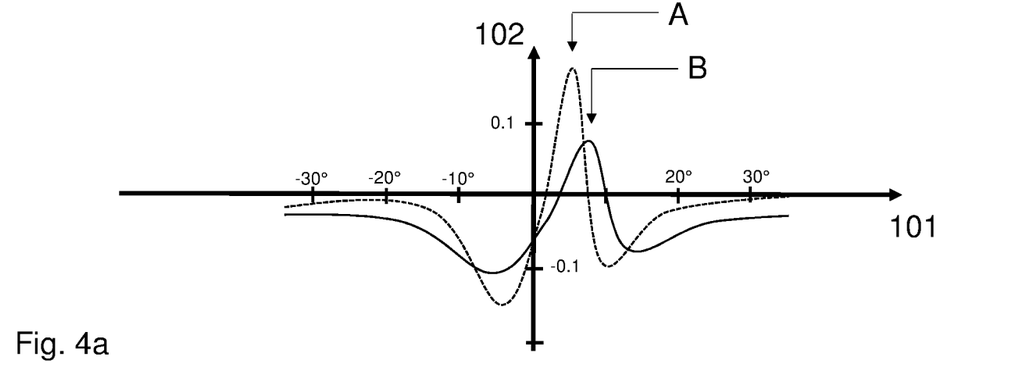
FIGS. 4a to 4c are a dependence of a measured strain in a ground compaction drum on its rotation angle under various conditions.
Figure 4B:
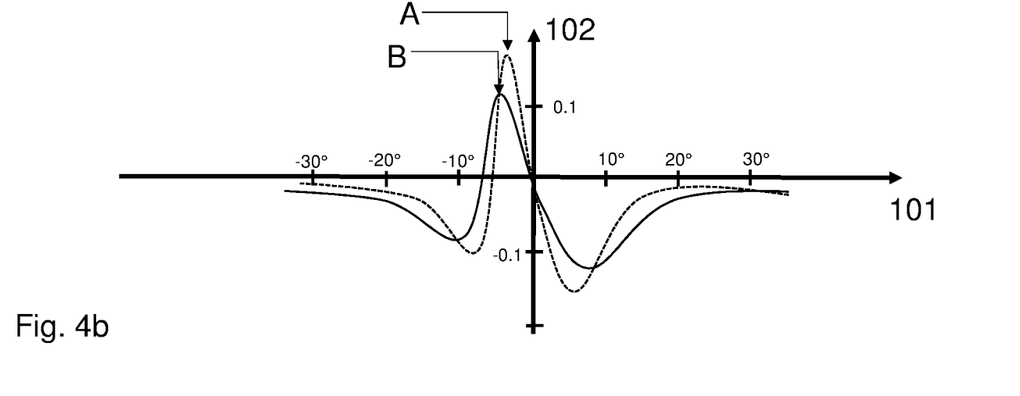
Figure 4C:
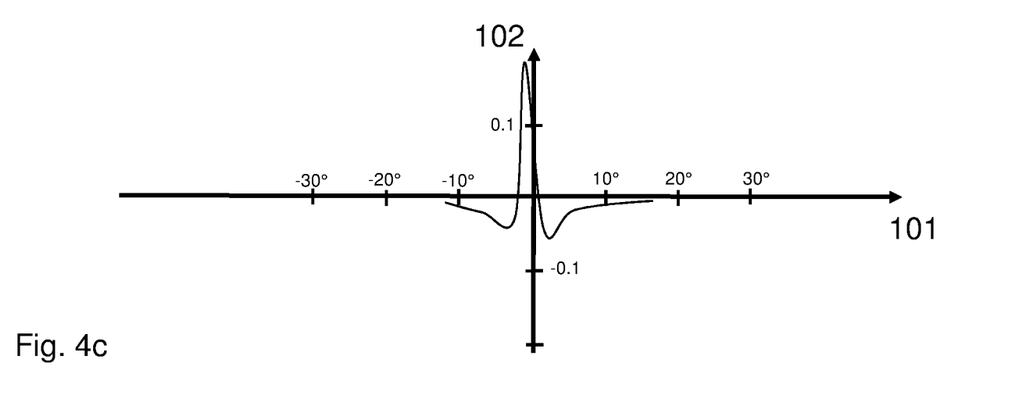

FIGS. 4a to 4c show the general progression of measured strains 102 as a function of the rotation angle 101 under various conditions. These general progressions were obtained as results of a test series in which the strain in a ground compaction drum 8 was measured. To this end, an articulated joint tandem roller of the BW138 type, which is manufactured by the applicant, was guided over the substrate U to be compacted. The roller had been provided with two-axis accelerometers of the AD22284 type for determining the rotation angle 101. Moreover, a strain sensor of the CST/300 type was screwed to the inner side of the rear ground compaction drum 8 in relation to the working direction a, which strain sensor provided the measured strains 102 depicted schematically here as general progressions.

FIG. 4a shows, in arbitrary units and as a function of the rotation angle 101, the deformations 102 measured when the roller was repeatedly guided over an asphalt surrogate. Here, the solid line represents the measured deformation behavior during a first passage over the asphalt surrogate, whereas the dotted line reflects the measured deformation behavior during a subsequent passage over the asphalt surrogate with an increased ground compaction. In each case, the roller moved in the working direction a. The two measured deformation progressions shown here are characterized by a critical rotation angle A, B at which the respective progressions reach a maximum. As is evident from FIG. 4a, the critical rotation angle A obtained during a subsequent passage and thus at a higher degree of stiffness shifts in relation to the critical rotation angle B obtained during the first passage. Further, it can be observed that during the second passage an absolute value of the measured maximum deformation 102, i.e. an amplitude of the measured deformation 102, has increased compared to the first passage.

FIG. 4b illustrates, in arbitrary units and as a function of the rotation angle 101, the deformations 102 measured when the roller was repeatedly guided over the asphalt surrogate. This test differs from that of FIG. 4a in that the roller here was moved over the substrate U against the working direction a, i.e. backwards. Both progressions result from a passage executed after the first passage, the degree of stiffness of the substrate U being greater in the case of the dotted line than in the case of the solid line. Based on the results of FIGS. 4b in combination with FIG. 4a, it can be concluded that the amplitude of the measured maximum deformation 102 increases as the ground compaction increases while the distance between the respective critical rotation angles A, B resulting during successive passages decreases with increasing ground compaction.

FIG. 4c shows, in arbitrary units and as a function of the rotation angle 101, the deformation measured when the roller was guided over a compact asphalt material, i.e. a material that could not be compacted any further. Compared with the progressions of FIGS. 4a and 4b, the amplitude of the measured maximum deformation is greater in the case of the compact asphalt material, as is a gradual change in the deformation with the rotation angle 101 in the region of the critical rotation angle A, B.

As a result of the progressions observed in FIGS. 4a to 4c, it can be stated that the degree of stiffness of the substrate U can be determined or inferred from a critical rotation angle A, B at which the measured strain 102 reaches a local maximum, a gradual progression of the measured strain 102 as a function of the rotation angle 101, and/or an absolute value of the measured maximum strain.

Figure 5:
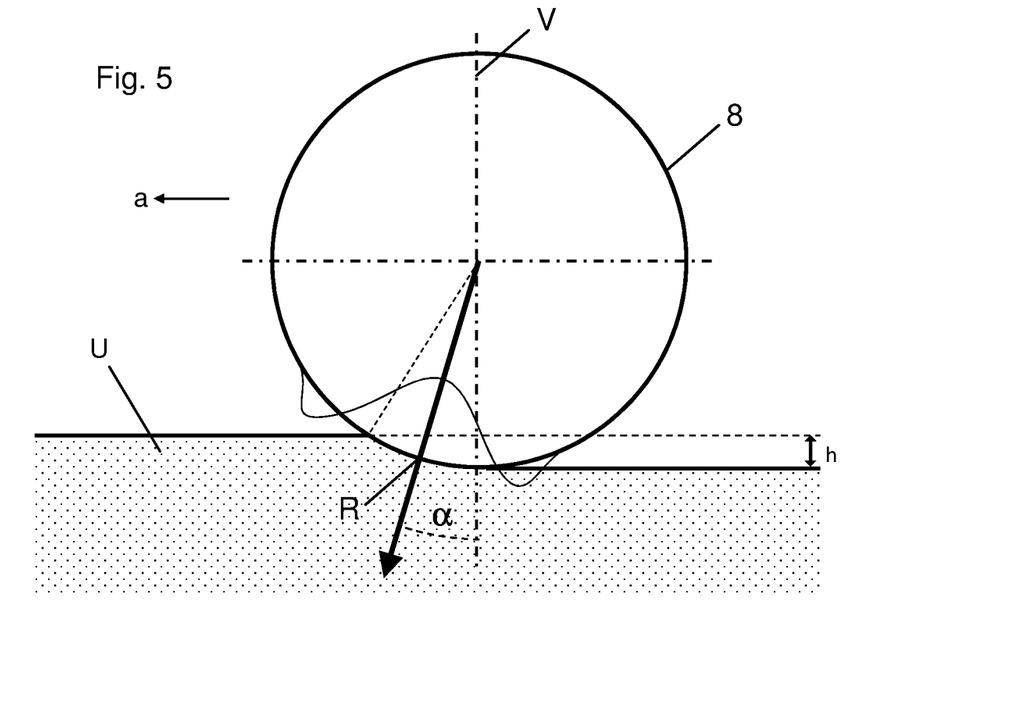
FIG. 5 is a side view of a ground compaction drum rolling over a substrate with a low stiffness.
Figure 6:
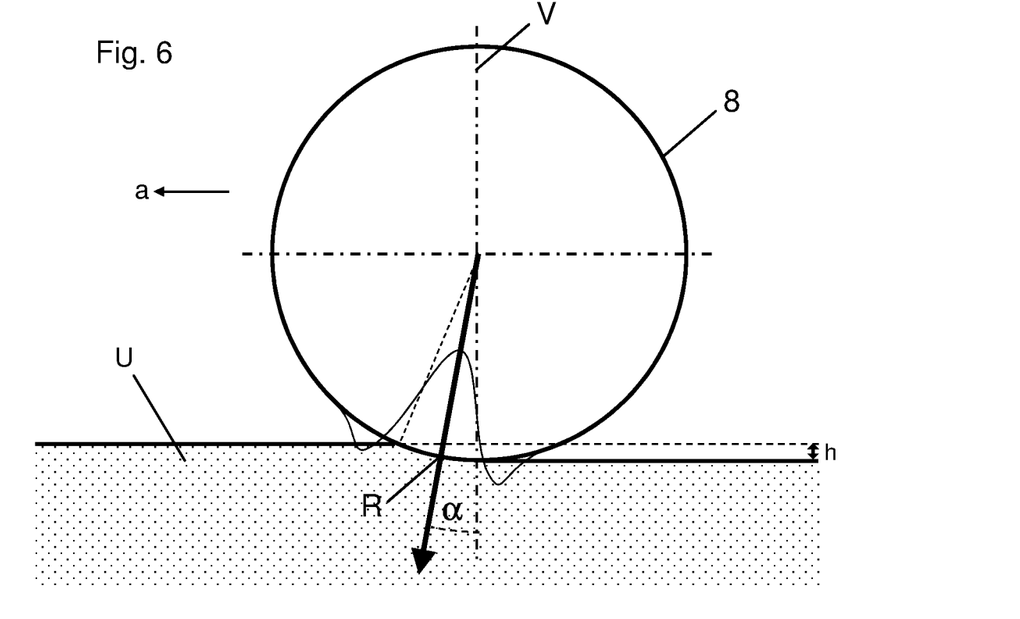
FIG. 6 is a side view of a ground compaction drum rolling over a substrate with a higher stiffness.

FIGS. 5 and 6 depict the process of rolling over a substrate U with a ground compaction drum 8 when the stiffness of the substrate U is low (FIG. 5) and when the stiffness of the substrate U is high (FIG. 6). For reasons of simplicity, it is assumed that the substrate has ideal plastic characteristics, which has proven a sufficient approximation in practice. The ground compaction drum 8 here moves in the working direction a from the right to the left over the substrate U. Due to the different levels of stiffness of the substrate U, the penetration depth h decreases with the increasing number of passages. The penetration depth h is also referred to as the settling measure. FIGS. 5 and 6 in particular show the determination of the point R of a maximum deformation on the circumference of the ground compaction drum 8 as well as the correlation between the position of the point R and the stiffness of the substrate U or the penetration depth h. In order to further illustrate this aspect of the invention, the progressions of the deformation over time, which are measured by the deformation sensor 11 and depicted in FIGS. 4a to 4c, are indicated by the curved lines in these figures. The dashed line extending from the rotation axis of the ground compaction drum 8 indicates the front edge of the deformation trough. The point R of maximum deformation is located approximately on the bisecting angle between the dashed line and the vertical reference line V. All in all, the deformation sensor 11 ascertains a point R of the circumference of the ground compaction drum 8 where the deformation is at a maximum. In the embodiment shown, this point R is indicated by the rotation angle a of the ground compaction drum 8, measured in relation to a vertical reference line V, e.g. the direction of the gravity vector. The rotation angle a can obviously also be indicated in relation to a different reference line, e.g. a horizontal straight line. What is important is that the position of the point R on the circumference of the ground compaction drum 8 is ascertained. As can be seen from a comparison of FIGS. 5 and 6, the rotation angle a between a line connecting the rotation axis of the ground compaction drum 8 with the point R on the circumference of the ground compaction drum 8 and the vertical reference line V becomes smaller with increasing stiffness of the substrate U. The rotation angle a is thus proportional to the penetration depth h. Since the point R approaches the vertical line extending from the rotation axis of the ground compaction drum 8 to the substrate U, the stiffness of the substrate U, or the contact state between the ground compaction drum 8 and the substrate U, can be inferred from the position of the point R. For example, the penetration depth h can be derived directly from the angle $\alpha$ and the drum radius r according to the following formula: $h = r \cdot (1 - \cos(2 \cdot \alpha))$. In the case of a drum radius r of, e.g., 500 mm, the settling measure or penetration depth h would be smaller than 0.5 mm for an angle $\alpha < 1.25°$ or smaller. At this stage, i.e. with a penetration depth h this small, an unreasonably high number of passages would have to be performed to achieve a measurable increase in compaction. Therefore, the compaction target has been accomplished. Besides permitting the identification of the end of the compaction process by recognizing that the measured angles a are becoming very small, it is also possible with the present invention to recognize that the bow wave preceding the ground compaction drum 8 is becoming too large. This is indicated by large angles a. This way, the operator of the ground compactor can initiate countermeasures in a timely manner before the bow wave becomes so large that the ground compaction drum 8 rolls over it and thus causes an unevenness in the road surface. As with the determination of the ground stiffness or the degree of compaction of the ground from the position of the point R of maximum deformation, it is preferred to perform the evaluation by means of characteristic diagrams for the angle a determined in advance for the identification of a bow wave that is too large. The evaluation is thus performed by means of empirically ascertained limits that are used to create the characteristic diagrams.

What is claimed is:

1. A ground compactor with a ground compaction drum rotating about a rotation axis during compaction of a substrate and an evaluation unit, wherein the ground compaction drum includes a deformation sensor for detecting an elastic deformation of the ground compaction drum, and in that the evaluation device is configured to determine the degree of stiffness of the substrate and/or the shape of a bow wave preceding the ground compaction drum in a working direction and/or the shape of a depression trough of the ground compaction drum based on the position of a point on a circumference of the ground compaction drum where the deformation sensor measures the largest deformation.

2. The ground compactor according to claim 1, wherein the ground compaction drum comprises an essentially hollow, cylindrical drum shell with an inner side facing the rotation axis, wherein the deformation sensor is arranged on said inner side of the drum shell.

3. The ground compactor according to claim 1, wherein the deformation sensor is designed to detect the elastic deformation in a section of the ground compaction drum.

4. The ground compactor according to claim 1, wherein the deformation sensor is a strain sensor for measuring a local strain in the ground compaction drum for measuring a local strain in the ground compaction drum occurring in the direction of rotation.

5. The ground compactor according to claim 1, wherein the ground compactor includes a measuring device for detecting a current rotation angle of the ground compaction drum.

6. The ground compactor according to claim 1, wherein the evaluation device is configured to use a rotation angle (α) spanned by a straight line intersecting the rotation axis and the point and a reference line, for example a horizontal or a vertical line, for ascertaining the degree of stiffness of the substrate and/or the shape of the bow wave and/or the shape of the depression trough.

7. The ground compactor according to claim 1, wherein the ground compactor includes at least one of the following devices:
an evaluation device for depicting results ascertained by the evaluation device and/or measured values detected by the deformation sensor as a function of the rotation angle; and/or
an input device for entering comments; and/or
a storage device for storing the measurement results and/or the comments.

8. The ground compactor according to claim 1, wherein the ground compactor includes an oscillating or static ground compaction drum.

9. The ground compactor according to claim 1, wherein a front ground compaction drum in relation to the working direction and a rear ground compaction drum in relation to the working direction comprise at least one deformation sensor.

10. The ground compactor according to claim 1, wherein the ground compactor is a tandem roller.

11. The method according to claim 10, wherein the first measuring step includes measuring a local strain of the ground compaction drum occurring in the direction of rotation of the ground compaction drum, as a measure of the elastic deformation of the ground compaction drum.

12. The method according to claim 11, wherein the degree of stiffness of the substrate and/or the shape of the bow wave and/or the shape of the depression trough are additionally determined by:
a gradual progression of the measured strain as a function of the rotation angle; and/or
an absolute value of the measured maximum strain.

13. The method according to claim 10, wherein a second measuring step includes ascertaining a rotation angle of the ground compaction drum, and an evaluation step includes depicting the elastic deformation in the ground compaction drum as a function of the rotation angle.

14. A method for determining the degree of stiffness of a substrate using a ground compactor according to claim 1, comprising the following steps:
moving a ground compactor with a ground compaction drum over the substrate; and
rotating the ground compaction drum about a rotation axis;
wherein
a first measuring step includes detecting an elastic deformation in at least a section of the ground compaction drum and the position of a point on a circumference of the ground compaction drum where the largest deformation occurs, wherein the degree of stiffness of the substrate and/or the shape of a bow wave preceding the ground compaction drum in a working direction and/or the shape of a depression trough of the ground compaction drum is determined from the position of said point.

* * * * *